US012765487B2

(12) United States Patent
Sha

(10) Patent No.: US 12,765,487 B2
(45) Date of Patent: Oct. 20, 2026

(54) RICE CULTIVAR 'PVL04'

(71) Applicant: The Board of Trustees of the University of Arkansas, Little Rock, AR (US)

(72) Inventor: Xueyan Sha, Stuttgart, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 383 days.

(21) Appl. No.: 18/540,629

(22) Filed: Dec. 14, 2023

(65) Prior Publication Data

US 2025/0194489 A1 Jun. 19, 2025

(51) Int. Cl.
*A01H 6/46* (2018.01)
*A01H 5/10* (2018.01)

(52) U.S. Cl.
CPC ............. *A01H 6/4636* (2018.05); *A01H 5/10* (2013.01)

(58) Field of Classification Search
None
See application file for complete search history.

(56) References Cited

U.S. PATENT DOCUMENTS

2020/0196551 A1* 6/2020 Linscombe .............. C12N 9/93

OTHER PUBLICATIONS

U.S. Plant Variety Protection Application No. 201700227, issued Jan. 29, 2020, Rice Cultivar PVL01, Louisiana State University Agricultural Center.
U.S. Plant Variety Protection Application No. 201900300, issued Nov. 30, 2020, Rice Cultivar PVL02, Louisiana State University Agricultural Center.
U.S. Plant Variety Protection Application No. 202400198, filed Dec. 14, 2023, Rice Cultivar PVL04, The Board of Trustees of the University of Arkansas.

* cited by examiner

*Primary Examiner* — Mykola V. Kovalenko
(74) *Attorney, Agent, or Firm* — Quarles & Brady, LLP

(57) ABSTRACT

A rice cultivar designated 'PVL04' is disclosed herein. The present invention provides seeds, plants, and plant parts derived from rice cultivar PVL04. Further, it provides methods for producing a rice plant by crossing PVL04 with itself or another rice variety. The invention also encompasses any rice seeds, plants, and plant parts produced by the methods disclosed herein, including those in which additional traits have been transferred into PVL04 through the introduction of a transgene, by breeding PVL04 with another rice cultivar, or by gene-editing rice cultivar PVL04.

26 Claims, No Drawings

RICE CULTIVAR 'PVL04'

BACKGROUND OF THE INVENTION

The present invention relates to a new and distinctive rice cultivar, designated 'PVL04' (having an experimental designation of 'RU2201021').

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in a region where rice is drill-seeded and a water-seeded nursery is used in regions where water-seeding is prominent.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

Rice, *Oryza sativa* L., is an important and valuable field crop. A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a novel rice cultivar designated PVL04. The invention encompasses the seeds, plants, and plant parts of rice cultivar PVL04, as well as plants with essentially all of the physiological and morphological characteristics of PVL04.

In another aspect, the present invention provides methods for controlling weeds in the vicinity of a rice plant of rice cultivar PVL04 using an acetyl CoA carboxylase (ACCase)-inhibiting herbicide. In some embodiments, the herbicide is applied post-emergence.

This invention also provides methods for producing a rice plant by planting a plurality of seeds or by crossing rice PVL04 with itself or another rice line. Any plant breeding methods using rice cultivar PVL04 are part of this invention, including selfing, backcrosses, hybrid production, and crosses to populations. All plants and seeds produced using rice cultivar PVL04 as a parent are within the scope of this invention, including gene-converted plants of PVL04. Methods for introducing a gene into PVL04, through traditional breeding, genetic transformation, or gene-editing are provided herein.

In still another aspect, the present invention provides regenerable cells for use in tissue culture of rice plant PVL04, as well as rice plants regenerated from these tissue cultures.

DEFINITIONS

To provide a clear and consistent understanding of the specification and claims, the following definitions are provided:

Allele. One of two or more alternative forms of a gene, all of which relate to a single trait or characteristic. In a diploid cell or organism, two alleles of a given gene occupy corresponding loci on a pair of homologous chromosomes.

Apparent starch amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation ($F_1$) hybrid may be crossed with one of the parental lines used to produce the $F_1$ hybrids.

Breeding. The genetic manipulation of living organisms.

Cell. As used herein, this term includes isolated cells, cells grown in tissue culture, and cells that comprise a plant or plant part.

Cultivar. Used interchangeably with "variety". Refers to plants that are defined by the expression of the characteristics resulting from a given genotype or combination of genotypes, distinguished from any other plant grouping by the expression of at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem and leaves.

F #. Denotes a filial generation, wherein the # is the generation number. For example, F1 is the first filial generation.

Gene. Refers to a unit of inheritance corresponding to a distinct sequence of DNA or RNA nucleotides that form part of a chromosome. A gene may encode a polypeptide or a nucleic acid molecule that has a function in the cell or organism.

Gene-converted. Describes a plant wherein essentially all of the desired morphological and physiological characteristics of a parental variety are maintained with the exception of a single trait that was transferred into the variety via backcrossing, genetic engineering, or gene-editing.

Genome (gene)-edited or genetically modified. Refers to a cell that includes a modification to its genome compared to a non-genome edited cell of the same type. In some cases, a non-genome edited cell is a wild-type cell.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the offspring or progeny of genetically dissimilar plant parents or stock produced as the result of controlled cross-pollination as opposed to a non-hybrid seed produced as the result of natural pollination.

Kernel length (L). Length of a rice grain, measured in millimeters.

Kernel width (W). Width of a rice grain, measured in millimeters.

Length/width (L/W) ratio. Determined by dividing the average length (L) by the average width (W).

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength".

Milling yield. The total amount of milled rice (whole and broken kernels) recovered after milling (i.e., removal of hulls, bran, and germ). In contrast, head rice yield is the total amount of whole kernels recovered after milling. Both values are expressed as a weight percentage of the original paddy or rough rice sample that was milled. For example, for a sample of 100 grams of rough rice, a milling yield of 65/70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as seeds, embryos, pollen, ovules, flowers, glumes, panicles, leaves, stems, nodes, buds, roots, root tips, anthers, pistils and the like.

Plant height. Measured in centimeters from the soil surface to the tip of the extended panicle at harvest.

Plant parts. Includes, without limitation, protoplasts, leaves, stems, nodes, buds, roots, root tips, anthers, pistils, seeds, grain, embryo, pollen, ovules, cotyledon, hypocotyl, pod, flower, shoot, tissue, petiole, cells, and meristematic cells.

Progeny. Includes an $F_1$ rice plant produced from the cross of two rice plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like. However, in preferred embodiments, it refers to true seeds.

Trait. Refers to an observable and/or measurable characteristic of an organism. For example, the present invention describes plants that have a trait that makes them resistant to quizalofop-p-ethyl herbicides, the generic name for ethyl ®-2-[4-(6-chloroquinoxalin-2-yl)oxy)phenoxy]propionate, which is sold under the tradename Provisia® (PV) herbicide. Quizalofop-p-ethyl herbicide belongs to the aryloxyphenoxy-propionates (FOP) herbicide chemical family (Weed Society Science of America Group 1), which control weeds by inhibiting the enzyme acetyl-CoA carboxylase (ACCase). PV rice is resistant to an ACCase-inhibiting herbicide.

Transgenic. Describes an organism or cell that contains genetic material that has been artificially introduced.

Wild-type. When made in reference to a gene, "wild-type" refers to a functional gene common throughout a plant population and, thus, arbitrarily designated the "normal" or "wild-type" form of the gene.

DETAILED DESCRIPTION OF THE INVENTION

The present invention provides a novel rice cultivar designated PVL04. The invention encompasses both the seeds of this cultivar and plants grown from these seeds.

Development and Characterization of Rice Cultivar PVL04

PVL04 (*Oryza sativa* L.) is a high yielding, early maturing, and short stature Provisia® (PV) long-grain rice variety developed at the Rice Research and Extension Center, University of Arkansas System Division of Agriculture (UA RREC) in Stuttgart, Arkansas. It was fast-track developed from the backcross BC2F1 of 18SIT0557*3/HPHI2 made in spring 2020. 18SIT0557 is an unreleased conventional long-grain rice line developed by UA RREC from the cross RU1102131/RU0903141, while HPHI2 is a proprietary mutant line owned by BASF (Ludwigshafen, Germany) with resistance to quizalofop-ethyl, an ACCase-inhibiting herbicide belonging to the aryloxyphenoxy-propionate (FOP) chemical family of herbicides. RU1102131 and RU0903141 are unreleased conventional long-grain lines developed by the Louisiana State University Agricultural Center H. Rouse Caffey Rice Research Station in Rayne, LA and Texas A&M AgriLife Research and Extension Center in Beaumont, TX, respectively. A timeline outlining how PVL04 was developed is provided in Table 1. The herbicide resistance trait of PVL04 is discussed further in the section titled "Herbicide Resistance" below.

TABLE 1

Developmental History of PVL04 (exp designation RU2201021) (18SIT0557*3/HPHI2)

| Year | Generation | Designation | Trials | Comments |
|---|---|---|---|---|
| 2019 | Initial cross | 19CRPV29 | Crossing | Spring |
| 2019 | Backcross | 19CRS1106 | Backcrossing | Summer |
| 2020 | Backcross | 20CRS1022 | Backcrossing | Spring |
| 2020 | BC2F1 | 20GH1022 | F1 plant | Greenhouse |

TABLE 1-continued

| Developmental History of PVL04 (exp designation RU2201021) (18SIT0557*3/HPHI2) | | | | |
|---|---|---|---|---|
| Year | Generation | Designation | Trials | Comments |
| 2020 | BC2F2 | 20A3887-3963 | F2 Space Plant | Puerto Rico |
| 2020-21 | BC2F3 | 20B3796 | Progeny row | Puerto |
| 2021 | BC2F4 | 21PSIT2035 | Provisia ® Advanced/ Elite Line Yield Trial (PAYT) | Rico |
| 2021-22 | BC2F5 | 21PSIT2035 | Purification and increase | Puerto |
| 2022 | BC2F5 | 22ARVAT E71 | Arkansas Rice Variety Advancement Trial (ARVAT) (6 locations) | Rico |
| 2022 | BC2F5 | 22PC E19 | Pre-commercial Trials (23 locations) | |
| 2022 | BC2F5 | RU2201021 | Uniform Regional Rice Nursery (4 locations) | |
| 2022 | BC2F5 | 22PAYT2107 | Provisia ® Advanced/ Elite Line Yield Trial (PAYT) | |
| 2022 | BC2F6 | RU2201021 | Breeder headrow increase | |
| 2022-23 | BC2F7 | RU2201021 | Breeder seed production | Puerto Rico |

PVL04 (used interchangeably with RU2201021) initiated as a bulk of a single BC2F3 progeny row 20B3796 at the winter nursery near Lajas, Puerto Rico in spring 2021. It was evaluated in 2021 Provisia® Advanced Elite Line Yield Trial (PAYT) as entry 21PSIT2035 at UA RREC and University of Arkansas System Division of Agriculture's Pine Tree Research Station (UA PTRS) near Colt, AR, and ranked the 2nd among 50 experimental PV lines and checks. In 2022, it was advanced to the Arkansas Rice Variety Advancement Trials (ARVAT), Pre-commercial Trials (PC), and the Cooperative Uniform Regional Rice Nurseries (URRN) with the experimental designation 'RU2201021' (Note: RU indicates that the trial was the URRN; 22 indicates that the year entered was 2022; 01 indicates that the location was Stuttgart, AR; and 021 indicates the entry number). The results of these performance trials for PVL04 are compared to those for other rice cultivars in the section titled "Performance Trial Results" below.

In 44 statewide and regional trials during 2021-2022, PVL04 yielded an average 187 bushels/acre (Bu/A) at 120 g kg-1 moisture as compared to 186 Bu/A of PVL03. Across state line, PVL04 out-yielded PVL03 in all five southern rice growing states except Louisiana. Average milling yields (g kg-1 whole milled kernels: g kg-1 total milled rice) were 605:690 for PVL04, compared to 598:700 of PVL03 (Table 2).

Average maturity of PVL04 is 88 days from emergence to reach 50% heading, which is about 2 days later than that of 'PVL03' (Table 2). PVL04 has a semi-dwarf plant type and is moderately susceptible to lodging but exhibits less lodging than PVL03. In yield tests across Mid-South, the average plant height of PVL04 was 40 inches, which is the same height as PVL03 (Table 2).

Inoculation of greenhouse plants with different races of blast pathogen (*Pyricularia oryzae*) indicate that PVL04 is resistant to blast races IB-1, IB-17, IB-49, and IE1-K, and moderately resistant to race IC-17 (Table 12). Molecular markers also confirmed that it possesses blast resistant genes Pi-kh and Pi-ta just like PVL03. Using the standard disease rating scale (R=resistant, MR=moderately resistant, MS=moderately susceptible, S=susceptible and VS=very susceptible to disease), PVL04 was rated as S to sheath blight (caused by *Rhizoctonia solani* Kühn) under artificial inoculation, MS to false smut (caused by *Ustilaginoidea virens* (Cooke) Takahashi) and narrow brown leaf spot (*Cercospora janseana*) under natural infestation, even though molecular marker analysis also confirmed that it has the resistance gene to narrow brown leaf spot.

Plants of PVL04 have erect culms, dark green erect leaves, and glabrous lemma, palea, and leaf blades. The lemma and palea are straw colored with purple apiculi, most of which fade to straw as grains approach maturity. PVL04 has a slender long grain longer than all predominant pureline varieties on the market, which include Diamond, DG263L, Cheniere, Presidio, PVL03, and CLL16. When measured by using a SeedCount (Stadvis Pty Ltd, Sydney, NSW, Australia), the milled whole kernel of PVL04 has an average length (L), width (W), and L/W ratio of 7.27 mm, 2.20 mm, and 3.31, as compared with 7.06, 2.28, and 3.10 of PVL03, 6.39, 2.34, and 2.74 of DG263L, and 6.93, 2.27, and 3.06 of CLL16, respectively (A. Famoso, personal communication, 2022).

The endosperm of PVL04 is nonglutinous, nonaromatic, and covered by a light brown pericarp. Similar to Cheniere, PVL04 is a southern long-grain with a L-202 type cooking quality, which is characterized by a high amylose content, intermediate gelatinization temperature, but a weak RVA profile (Webb, 1985). Average apparent amylose content of PVL04 is 24.5 g kg-1 and gelatinization temperature of 70.5° C.

Breeder and seed increase plots of PVL04 were rogued several times throughout the season. The original release of breeder head row may contain the following variants in any combination: taller, shorter, earlier, later, glabrous or pubescent plants, golden and black hull, sterile panicle, as well as short-, medium-, intermediate- or very-long slender grains. Other atypical plants may still be encountered in the variety. The total variants and/or off-types numbered less than 1 per 2500 plants.

The above-mentioned characteristics of rice cultivar PVL04 are based primarily on data collected in Stuttgart, Arkansas. The results of the rice performance trials (ARVAT 2022, PAYT 2021-2022, URRN 2022, and PC 2022) are detailed in Tables 2-9. Grain quality data is presented in Table 10.

Performance Trial Results

TABLE 2

| Overall average grain yield (12% moisture), milling yield, and agronomic characteristics (2020-2022) | | | | | | | |
|---|---|---|---|---|---|---|---|
| | Grain | Grain | Milling Yield (%) | | Days to | Plant | Lodging |
| Variety | Yield (Bu/A) | Yield (Lb/A) | Head Rice | Total Rice | 50% heading | height (inch) | incidence (%) |
| RU2201021 | 187 | 8,430 | 60.5 | 69 | 88 | 40 | 0.2 |
| PVL03 | 186 | 8,358 | 59.8 | 70 | 86 | 40 | 0.3 |
| No. trials | 44 | 44 | 27 | 27 | 28 | 30 | 44 |

TABLE 3

2022 ARVAT Grain yield by location collected from six Arkansas locations (Dr. Jarrod Hardke, personal communication, 2022)

| | Grain yield (Bu/A at 12% $H_2O$) by location | | | | | | |
|---|---|---|---|---|---|---|---|
| Variety | Clay[a] | Desha | NEREC | PTRS | RREC | NERREC | Mean |
| RU2201021 | 166 | 187 | 177 | 185 | 182 | 156 | 175 |
| PVL03 | 186 | 172 | 156 | 168 | 183 | 166 | 172 |

[a]Test location: Clay = Clay Co., AR., Desha = Desha, Co., AR., NEREC = Northeast Research and Extension Center at Keiser, AR., PTRS = Pine Tree Research Station near Colt, AR., RREC = Rice Research and Extension Center near Stuttgart, AR., and NERREC = Northeast Rice Research and Extension Center, Harrisburg, AR

TABLE 4

2022 ARVAT Average days to 50% heading, plant height, and milling yield data collected from 6 Arkansas locations (Dr. Jarrod Hardke, personal communication, 2022)

| Variety | Days to 50% heading | Plant height (inch) | % Head rice/ % Total rice |
|---|---|---|---|
| RU2201021 | 90 | 38 | 63/71 |
| PVL03 | 88 | 38 | 60/71 |

TABLE 5

2022 PAYT Average agronomic data and yield data by location

| | Days to 50% | Plant height | Milling Yield (% HR: | Grain yield (Bu/A) by location | | | | |
|---|---|---|---|---|---|---|---|---|
| Variety | heading | (in) | % TR) | NE[a] | PTRS | RB1 | RB2 | Mean |
| RU2201021 | 92 | 42 | 63/69 | 210 | 196 | 183 | 226 | 206 |
| PVL03 | 90 | 42 | 63/70 | 184 | 167 | 192 | 199 | 192 |
| $LSD_{0.05}$[b] | 1.1 | 1 | 0.7/0.5 | 22.9 | 14.8 | 16.5 | 17.1 | 9.5 |

[a]Test location: NE = Northeast Research and Extension Center, PTRS = Pine Tree Research Station, RB = Rice Research and Extension Center
[b]Least significant difference at 5% level

TABLE 6

2021 PAYT Agronomic and yield data by location

| | Days to 50% | Plant height | Milling yield (% HR/ | Grain yield (Bu/A) by location | | |
|---|---|---|---|---|---|---|
| Variety | heading | (inch) | % TR) | PTRS[a] | RREC | Mean |
| RU2201021 | 86 | 42 | 54/65 | 214 | 211 | 212 |
| PVL03 | 85 | 42 | 56/64 | 200 | 200 | 200 |
| $LSD_{0.05}$[b] | 1.8 | 1.7 | 1.6/1.0 | 17.6 | 13.4 | 11.5 |

[a]Test location: PTRS = Pine Tree Research Station, RREC = Rice Research and Extension Center
[b]Least significant difference at 5% level

TABLE 7

2022 URRN Average Agronomic data and yield data by state

| | Days to 50% | Plant height | Milling yield (% HR/ | Grain yield (Bu/A) by state | | | | |
|---|---|---|---|---|---|---|---|---|
| Variety | heading | (inch) | % TR) | AR[a] | LA | MS | TX | Mean |
| RU2201021 | 83 | 40 | 54/69 | 201 | 173 | 215 | 116 | 176 |
| PVL03 | 81 | 40 | 51/69 | 216 | 197 | 195 | 142 | 188 |

[a]Tested in Stuttgart, AR, Crowley, LA, Stoneville, MS, and Beaumont, TX

TABLE 8

2022 PC Average agronomic and yield data collected from 23 locations

| | Days to 50% | Plant height | Lodging | Milling yield (% HR/ | Grain yield (Bu/A) by location | | |
|---|---|---|---|---|---|---|---|
| Variety | heading | (inch) | (%) | % TR) | AR[a] | LA | Mean |
| RU2201021 | 86 | 41 | 0.5 | 62/69 | 179 | 191 | 185 |
| PVL03 | 84 | 41 | 0.6 | 62/70 | 176 | 204 | 188 |

[a]Arkansas (AR), Louisiana (LA), and Texas, (TX)

TABLE 9

2022 Horizon Ag Provisia ® Yield Trial Average yield and rank by location (20 entries per location) (Dr. Tim Walker, personal communication, 2022)

| | Average yield | Average rank (out | Rank by location (out of 20) | | | | |
|---|---|---|---|---|---|---|---|
| Variety | (bu/A) | of 20) | AR1[a] | AR2 | MO1 | MO2 | MS |
| RU2201021 | 190 | 2.8 | 1 | 2 | 1 | 3 | 7 |
| PVL01 | 158 | 16.4 | 19 | 16 | 19 | 11 | 17 |
| PVL02 | 117 | 19.6 | 20 | 20 | 20 | 20 | 18 |
| PVL03 | 177 | 10 | 15 | 12 | 9 | 13 | 1 |

[a]Test location: AR1 = Northeast Rice Research and Extension Center, Harrisburg, AR., AR2 = Rice Research and Extension Center near Stuttgart, AR., MO1 = Fisher Delta Research, Extension and Education Center, Portageville, MO., MO2 = The Missouri Rice Research and Merchandising Council Farm, Malden, MO, MS = Delta Research and Extension Center, Stoneville, MS

TABLE 10

Kernel dimensions of milled whole kernel and chalkiness analyzed with a SeedCount (Stadvis Pty Ltd, Sydney, NSW, Australia) on the Cooperative Uniform Rice Regional Nursery conducted in Crowley, LA, 2022 (courtesy of Dr. Adam Famoso).

| Variety | Length (L) mm | Width (W) mm | L/W ratio | Chalky kernel % | Chalk impact |
|---|---|---|---|---|---|
| RU2201021 | 7.27 | 2.20 | 3.31 | 13.40 | 18.20 |
| PVL03 | 7.06 | 2.28 | 3.10 | 15.30 | 18.60 |

TABLE 11

| Distinguishing Characteristics of Morphology and Physiology |
|---|
| Plant: |
| Grain type: Long<br>Days to maturity (Seeding to 50% heading): 88 (range 79-90 days)<br>Plant height: 102 cm (range 90-115 cm)<br>Plant color (at booting): Dark green<br>Culm: |
| Angle (degrees from perpendicular after flowering):<br>Erect (less than 30°)<br>Flag leaf (after heading): |
| Pubescence: Glabrous<br>Leaf angle (after heading): Erect<br>Blade color (at heading): Dark green<br>Panicle: |
| Length: 21.1 cm<br>Type: Compact<br>Exsertion (near maturity): Moderately well<br>Axis: Droopy<br>Shattering (at maturity): Low (1-5%)<br>Grain (spikelet): |
| Awns (after full heading): Absent<br>Apiculus color: Purple<br>Stigma color: Light Green and Purple<br>Lemma and palea color (at maturity): Straw<br>Lemma and palea pubescence: Glabrous<br>Grain (seed): |
| Seed coat color: Light brown<br>Scent: Nonscented<br>Shape class (length/width ratio): |
| Paddy: Long (3.4:1 and more)<br>Brown: Long (3.1:1 and more)<br>Milled: Long (3.0:1 and more) 3.33<br>Size: 18.5 g/1000 seeds milled rice<br>Disease resistance: |
| Rice blast (*Pyricularia grisea* (Cooke) Sacc.): Moderately resistant<br>Sheath blight (*Rhizoctonia solani* Kuhn): Susceptible<br>False smut (*Ustilaginoidea virens* (Cooke) Takah.):<br>Moderately susceptible<br>Bacterial panicle blight (*Burkholderia glumae* and *B. gladioli*): Susceptible<br>Narrow brown leaf spot (Cercospora janseana):<br>Moderately susceptible |

Disease Evaluations of Rice Cultivar PVL04

Varietal resistance is the most efficient and reliable means of controlling rice diseases. Conservation and improvement of disease resistance is a continuous endeavor basic to varietal development. Incorporation of existing and new resistance sources is a complex process limited by several variables. The rice disease research program routinely evaluates breeding program entries to provide disease data required for superior variety development. Our objectives are to increase varietal disease resistance and to define disease liabilities of new varieties released for rice production in Arkansas.

Rice diseases are mostly rated visually on a 0-9 scale to estimate degree of severity. Numerical data is often converted to this scale. A rating of zero indicates complete disease immunity. A rating of one to three indicates resistance where little loss occurs and in the case of rice blast pathogen growth is restricted considerably. Conversely, a nine rating indicates maximum disease susceptibility, which typically results in near complete plant death and/or yield loss. Depending upon the disease in question, a disease rating of four to six is usually indicative of acceptable disease resistance under conditions slightly favoring the pathogen. Numerical ratings are sometimes converted to letter symbols where 0-3=R (resistant), 3-4=MR (moderately resistant), 5-6=MS (moderately susceptible) 7=S (susceptible) and 8-9 VS (very susceptible). Exceptions to established ratings do occur unexpectedly as disease situations change.

These data come from several sources. Advanced and promising breeding lines are normally evaluated by researchers in other states. It is not unusual for ratings to vary with location and year due to environmental differences and research procedures. Ratings within a source traditionally have been consistent.

Greenhouse blast tests are the primary means of screening large number of entries for varietal reaction to the many blast races occurring in the production areas. Although results are quite variable and testing conditions tends to overwhelm any field resistance present in the entry, this test provides an accurate definition of the fungus-variety genetics. Blast field nurseries, utilizing both natural and lab produced inoculum, are established in an effort to better define blast susceptibility under field conditions. Since field nursery is also quite variable, new techniques are currently being developed and evaluated to better estimate cultivar field resistance to blast.

Field nurseries are established and artificially inoculated to provide a uniform disease pressure for evaluations under field conditions. Grower nurseries are established operate in an effort to evaluate disease reactions in grower fields under current production practices. Over time these nurseries document variety performance under adverse disease conditions in Arkansas production fields.

Below, Tables 12-13 show disease evaluation data collected for RU2201021.

TABLE 12

Summary of available leaf blast (*Pyricularia oryzae*) rating data from plants inoculated with the indicated race using standard greenhouse techniques, 2022 (3 replications)

| Variety | IB-1[a] | IB-17 | IB-49 | IC-17 | IE1-K |
|---|---|---|---|---|---|
| RU2201021 | R | R | R | MR | R |
| PVL03 | R | MR | R | MR | MR |
| No. trials | 1 | 1 | 1 | 1 | 1 |

[a]Disease reaction,
R = resistant,
MR = moderately resistant,
MS = moderately susceptible, and
S = susceptible.
Note:
RU2201021 has the Pi-ta and Pi-kh genes for blast resistance.

TABLE 13

RU2201022 Reactions[a] to diseases and lodging (2022)

| Variety | Sheath Blight | Blast | Straight-head | Bacterial Panicle Blight | Narrow Brown Leaf Spot | Stem Rot | Kernel Smut | False Smut | Lodging | Black Sheath Rot | Sheath Spot |
|---|---|---|---|---|---|---|---|---|---|---|---|
| RU2201021 | S | — | — | — | MS | — | MS | — | — | — | — |

[a]Reaction: R = Resistant; MR = Moderately Resistant; MS = Moderately Susceptible; S = Susceptible; VS = Very Susceptible (cells with no values indicate no definitive Arkansas disease rating information is available at this time). Reactions were determined based on recent observations from test plots across Arkansas. In general, these ratings represent expected cultivar reactions to disease under conditions that most favor severe disease development.
Table prepared by Y. Wamishe, Associate Professor/Extension Plant Pathologist.

Herbicide Resistance

Provisia® (PV) rice is resistant to aryloxyphenoxy-propionates (FOP) herbicides (Weed Society Science of America Group 1), which control weeds by inhibiting the enzyme acetyl-CoA carboxylase (ACCase). PV rice was developed through mutagenesis of the ACCase locus using traditional breeding techniques and is not considered genetically modified. The herbicide-resistance trait of this rice makes it particularly useful in regions where there is a need to control weedy rice and other tough grasses. While the majority of rice cultivars planted in the southern United States are Clearfield® (CL) inbred or hybrid, which rely on inhibiting the enzyme acetohydroxyacid synthase (AHAS), also called acetolactate synthase (ALS), agronomic practices that include rotating different herbicide modes of action is beneficial for mitigating herbicide resistance of targeted weed species. This strategy requires alternate planting of rice cultivars containing different herbicide-resistance traits. PV rice can be used as one such alternate cultivar.

The plants of rice cultivar PVL04 have increased tolerance or resistance to ACCase-inhibiting herbicides, particularly aryloxyphenoxy-propionate herbicides. Thus, the plants of rice cultivar PVL04 are herbicide-tolerant or herbicide-resistant rice plants. An "herbicide-tolerant" or a "herbicide-resistant" rice plant is a rice plant that is tolerant or resistant to at least one herbicide at a level that would normally kill or inhibit the growth of a normal or wild-type rice plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Likewise, the terms "aryloxyphenoxy-propionate-tolerant" and "aryloxyphenoxy-propionate-resistant" are used interchangeably and are intended to be of an equivalent meaning and an equivalent scope as the terms "aryloxyphenoxy-propionate-tolerance" and "aryloxyphenoxy-propionate-resistance", respectively.

Accordingly, the present invention also provides rice plants, plant tissues, or plant cells treated with an ACCase-inhibiting herbicide. ACCase-inhibiting herbicides include, without limitation, an aryloxyphenoxy-propionate herbicide (FOP), a cyclohexanedione herbicide (DIM), a phenylpyrazoline herbicide, an agronomically acceptable salt or ester of one of these, or a mixture thereof. In some embodiments, the ACCase-inhibiting herbicide is an aryloxyphenoxy-propionate herbicide or a mixture of two or more aryloxyphenoxy-propionate herbicides. In one embodiment, the ACCase-inhibiting enzyme is Quizalofop-ethyl.

Suitable aryloxyphenoxy-propionate herbicides (FOPs) include, without limitation, ASSURER II HERBICIDE (Quizalofop-ethyl), DYNOFOP (Clodinafop-propargyl), BEAUTY (Cyhalofop-butyl), KEYLOFOB (Diclofop-methyl), ACCLAIM (Fenoxaprop-ethyl), JOKER (Fenthiaprop), FUSILADE (Fluazifop-butyl), a derivative of any of the aforementioned herbicides, and a mixture of two or more of the aforementioned herbicides. More specifically, the aryloxyphenoxy-propionate herbicide can be selected from, but is not limited to, ethyl (R)-2-[4-(6-chloroquinoxalin-2-yloxy)phenoxy]propionate, prop-2-ynyl (R)-2-[4-(5-chloro-3-fluoro-2-pyridyloxy)phenoxy]propionate, butyl (R)-2-[4-(4-cyano-2-fluorophenoxy)phenoxy]propionate, methyl (RS)-2-(4-(2,4-dichlorophenoxy)phenoxy)propionate, ethyl (RS)-2-[4-(6-chloro-1,3-benzoxazol-2-yloxy)phenoxy]propionate, (RS)-2-[4-(6-chloro-1,3-benzothiazol-2-yloxy)phenoxy]propionic acid, and butyl (RS)-2-{4-[5-(trifluoromethyl)-2-pyridyloxy]phenoxy}propionate.

Examples of cyclohexanedione herbicides (DIMs) include but are not limited to: cycloxydim, sethoxydim, clethodim, or tepraloxydim. Examples of phenylpyrazoline herbicides include but are not limited to pinoxaden.

Preferred esters of quizalofop or quizalofop-P include the ethyl and tefuryl esters; and preferred esters of haloxyfop or haloxyfop-P include the methyl and etotyl esters.

In other embodiments, the herbicide may be a mixture of a one or more aryloxyphenoxy-propionates with an herbicide having another mode of action (e.g., chlorophyll/carotenoid pigment inhibitors, cell membrane disruptors, photosynthesis inhibitors, cell division inhibitors, root inhibitors, shoot inhibitors, and combinations thereof.)

A wide variety of formulations can be employed for protecting plants from weeds to enhance plant growth and reduce competition for nutrients. Customary formulations include ready-to-spray aqueous solutions, powders, or suspensions; as concentrated or highly concentrated aqueous, oily, or other solutions, suspensions, or dispersions; as emulsions, oil dispersions, pastes, dusts, granules, or other broadcastable formats. The use form depends on the particular intended purpose. However, in each case, it should ensure a fine and even distribution of the compound. The present invention provides a method for controlling weeds in a field, said method comprising: growing a plant according to the present invention in a field; and contacting said plant, including plant tissues and plant cells, and weeds in the field with an effective amount of an ACCase-inhibiting herbicide to which the plant, plant tissues, and plant cells are tolerant, thereby controlling weeds in the field without adversely affecting the cultivated rice plant, plant tissues, and plant cells. Herbicides or herbicidal compositions can be applied post-emergence, e.g., using over-the-top application, pre-planting, or together with the seed to control weeds in areas surrounding the rice plants described herein. Herbicides or herbicidal formulations can be applied, e.g., as foliar treatments or soil treatments, in accordance with conventional methods, e.g., by spraying, atomizing, dusting, spreading, watering, or co-planting in admixture with the seed. The herbicidal compositions can be applied diluted or undiluted.

An herbicide can be used by itself or an herbicide formulation can be used that contains other additives. Additives that may be found in an herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. Such formulations are prepared in a known manner, for example by extending the active compound with auxiliaries suitable for the formulation of agrochemicals, such as solvents and/or carriers, emulsifiers, surfactants and dispersants, preservatives, antifoaming agents, anti-freezing agents, and also optionally colorants and/or binders and/or gelling agents.

Methods

This present invention provides methods for producing rice plants. In some embodiments, these methods involve planting a plurality of rice seeds provided herein under conditions favorable for the growth of rice plants.

The plants of rice cultivar PVL04 have increased resistance to ACCase-inhibiting herbicides, particularly aryloxyphenoxy-propionate herbicides, and thus find use in methods for controlling weeds. Accordingly, the present invention provides methods for controlling weeds in the vicinity of a rice plant of rice cultivar PVL04. The ACCase-inhibiting herbicide may be selected from the group consisting of an aryloxyphenoxy-propionate herbicide (FOP), a cyclohexanedione herbicide (DIM), a phenylpyrazoline herbicide, an agronomically acceptable salt or ester of one of these, or a mixture thereof. However, in preferred embodiments, the ACCase-inhibiting herbicide is an aryloxyphenoxy-propionate herbicide or a mixture of two or more aryloxyphenoxy-propionate herbicides.

The herbicides or herbicidal formulation can be applied, e.g., as foliar treatments, in accordance with any application method known in the art including, but not limited to, spraying, atomizing, dusting, spreading, watering, or co-planting in admixture with the seed. In some embodiments, the herbicide is applied pre-emergence or before sowing and/or after pregermination. "Pregermination" refers to a process in which seeds are sprouted in the absence of soil. Thus, the phrase "after pregermination" refers to the period of development after germination has occurred (i.e., after the root penetrates through the seed coat). In other embodiments, the herbicide is applied to the weeds and to the rice plant, plant tissues, and plant cells post-emergence, i.e., after the weeds and crop have emerged from the soil, preplanting, or together with the seed. These treatments either can be applied in a broadcast or directed fashion. Notably, for post-emergence applications it is often advantageous to combine the herbicide with a surfactant to facilitate maximum coverage of the weed with the solution. Additives found in an aryloxyphenoxy-propionate herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates, and liquid concentrates. The herbicide and herbicide formulations can be applied in accordance with conventional methods, for example, by spraying, irrigation, dusting, or the like.

For the methods of the present invention, the preferred amount or concentration of the herbicide is an "effective amount" or "effective concentration", i.e., an amount or concentration that is sufficient to kill or inhibit the growth of a similar wild-type rice plant, rice plant tissue, rice plant cell, or rice seed, but that does not kill or inhibit as severely the growth of the herbicide-resistant plants, plant tissues, plant cells, and seeds. Typically, the effective amount of an herbicide is an amount that is routinely used in agricultural production systems to kill weeds of interest. Such amounts are known to those of ordinary skill in the art. The concentration of the herbicide(s) present in the herbicidal formulation can be varied within wide ranges. In general, the formulations comprise approximately from 0.001% to 98% by weight, preferably 0.01 to 95% by weight of at least one active ingredient. In some embodiments, the herbicide(s) is employed in a purity of from 90% to 100%, preferably 95% to 100% (as measured, e.g., by NMR or IR spectra). %

The phrase "control of undesired vegetation" refers to the killing of weeds and/or otherwise retarding or inhibiting the normal growth of the weeds. A "weed" is any plant that grows in a location where it is undesired. The weeds of the present invention can include crop plants that are growing in an undesired location. For example, a soybean plant that is in a field that predominantly comprises rice plants can be considered a weed, if the soybean plant is undesired in the field of rice plants. Another example of a weed is red rice, which is the same species as cultivated rice.

The weeds that may be treated include, for example, dicotyledonous and monocotyledonous weeds. Monocotyledonous weeds include, but are not limited to, weeds of the genera: *Echinochloa, Brachiaria, Zea, Digitaria, Eleucine, Sorghum, Panicum, Oryza, Leptochloa, Cynodon, Setaria, Phleum, Poa, Festuca, Lolium, Bromus, Avena, Cyperus, Agropyron, Monochoria, Fimbristyslis, Sagittaria, Eleocharis, Scirpus, Paspalum, Ischaemum, Sphenoclea, Dactyloctenium, Agrostis, Alopecurus, Canadaspis*, and *Apera*. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solammm, Rorippa, Rotala, Lindernia, Lamium, Veronica, Abutilon, Emex, Datura, Viola, Galeopsis, Papaver, Centaurea, Trifolium, Ranunculus, Centrosaurus*, and *Taraxacum*.

The weeds may include species of annual grasses, perennial grasses, or weedy rice. Examples of annual grasses include, but are not limited to, Barnyardgrass (*Echinochloa crus-galli*), Barnyardgrass, Late (*Echinochloa oryzicola*), Broadleaf Signalgrass (*Brachiaria platyphylla*), Corn (*Zea mays*), Crabgrass, Large (*Digitaria sanguinalis*), Crabgrass, Smooth (*Digitaria ischaemum*), Goosegrass (*Eleucine indica*), Johnsongrass, Seedling (*Sorghum halepense*), Junglerice (*Echinochloa colona*), *Panicum*, Fall (*Panicum dichtomiflorum*), *Panicum*, Texas (*Panicum texamum*), Rice, Red (*Oryza sativa*), Shattercane (*Sorghum bicolor*), Sprangeletop (*Leptochloa* spp.), Witchgrass (*Panicum capillare*), and volunteer rice, such as conventional rice and hybrid rice. Examples of perennial grasses include, but are not limited to, Bermudagrass (*Cynodon dactylon*) and Johnsongrass, Rhizome (*Sorghum halepense*). Examples of red/weedy rice include, but are not limited to, *Oryza longistaminata, Oryza sativa* L. var. *sylvatica, Oryza latifolia, Oryza barthii* A. Chev, *Oryza punctata*, and *Oryza rufipogon*.

In these methods, the ACCase-inhibiting herbicide or herbicidal formulation can be applied, e.g., as foliar treatments, in accordance with any application method known in the art including, but not limited to, spraying, atomizing, dusting, spreading, watering, or co-planting in admixture with the seed. Prior to application, the ACCase-inhibiting herbicide can be converted into the customary formulations, for example ready-to-spray aqueous solutions, powders, or suspensions; as concentrated or highly concentrated aqueous, oily, or other solutions, suspensions, or dispersions; as emulsions, oil dispersions, pastes, dusts, granules, or other broadcastable formats. The use form depends on the particular intended purpose. However, in each case, the use form should ensure a fine and even distribution of the active herbicide compound.

The formulations are prepared in a known manner (see, e.g., U.S. Pat. No. 3,060,084, EP-A 707 445 (for liquid concentrates), Browning, "Agglomeration", Chemical Engineering, pp. 147-48 (Dec. 4, 1967); Perry's Chemical Engineer's Handbook, 4th Ed., McGraw-Hill, New York, pp. 8-57 (1963), and et seq.; PCT Publication No. WO 91/13546; U.S. Pat. Nos. 4,172,714; 4,144,050; 3,299,566; 3,920,442; 5,180,587; 5,232,701; and 5,208,030; G.B. U.S. Pat. No. 2,095,558; Klingman, "Weed Control as a Science", John Wiley and Sons, Inc., New York (1961); Hance et al., Weed Control Handbook, 8th Ed., Blackwell Scientific Publications, Oxford (1989); Mollet, H., Grubemann, A., Formulation technology, Wiley VCH Verlag GmbH, Weinheim, Germany (2001); and D. A. Knowles, Chemistry and Technology of Agrochemical Formulations, Kluwer Academic Publishers (ISBN 0-7514-0443-8), Dordrecht (1998)), for example by extending the active compound with auxiliaries suitable for the formulation of agrochemicals, such as solvents and/or carriers, and, if desired, emulsifiers, surfactants and dispersants, preservatives, antifoaming agents, anti-freezing agents, colorants, binders, and/or gelling agents.

Examples of suitable solvents include water, aromatic solvents (e.g., Solvesso products, xylene), paraffins (e.g., mineral oil fractions), alcohols (e.g., methanol, butanol, pentanol, benzyl alcohol), ketones (e.g., cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used. Examples of suitable carriers are ground natural minerals (e.g., kaolins, clays, talc, chalk) and ground synthetic minerals (e.g., highly disperse silica, silicates). Suitable emulsifiers are nonionic and anionic emulsifiers (e.g., polyoxyethylene fatty alcohol ethers, alkylsulfonates, arylsulfonates). Examples of dispersants are lignin-sulfite waste liquors and methylcellulose.

Suitable surfactants used are alkali metal, alkaline earth metal, and ammonium salts (e.g., of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids, and sulfated fatty alcohol glycol ethers), condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors, and methylcellulose.

Substances that are suitable for the preparation of directly sprayable solutions, emulsions, pastes, or oil dispersions include mineral oil fractions of medium to high boiling point (e.g., kerosene or diesel oil); coal tar oils and oils of vegetable or animal origin; aliphatic, cyclic, and aromatic hydrocarbons (e.g., toluene, xylene, paraffin, tetrahydronaphthalene, alkylated naphthalenes or their derivatives), methanol, ethanol, propanol, butanol, cyclohexanol, cyclohexanone, isophorone, highly polar solvents (e.g., dimethyl sulfoxide, N-methylpyrrolidone), and water. Additional substances that can be added to the formulation include anti-freezing agents (e.g., glycerin, ethylene glycol, and propylene glycol) and bactericides. Suitable antifoaming agents include, for example, antifoaming agents based on silicon or magnesium stearate. Suitable preservatives include, for example, dichlorophen and enzylalkoholhemiformal. Seed treatment formulations may additionally comprise binders and optionally colorants.

Binders can be added to improve the adhesion of the active materials after treatment. Suitable binders include, for example, block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (LUPASOL, POLYMIN), polyethers, polyurethans, polyvinylacetate, tylose, and copolymers derived from these polymers.

Optionally, colorants can be included in the formulation. Suitable colorants or dyes for treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, and basic red 108. An example of a suitable gelling agent is carrageen (SATIAGEL).

Powders, materials for spreading, and dustable products can be prepared by mixing or concomitantly grinding the active substances with a solid carrier. Granules (e.g., coated granules, impregnated granules, and homogeneous granules) can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers (e.g., ammonium sulfate, ammonium phosphate, ammonium nitrate), urea, and products of vegetable origin (e.g., cereal meal, tree bark meal, wood meal, nutshell meal, cellulose powders).

In general, the formulations comprise the ACCase-inhibiting herbicide at a concentration of from 0.001% to 98% by weight of active compound, preferably 0.01 to 95% by weight. In this case, the ACCase-inhibiting herbicides are employed in a purity of 90% to 100% by weight, preferably 95% to 100% by weight (according to NMR spectrum).

The ACCase-inhibiting herbicide can be used in the form of directly sprayable solutions, powders, suspensions or dispersions, emulsions, oil dispersions, pastes, dustable products, materials for spreading, or granules, by means of spraying, atomizing, dusting, spreading or pouring the herbicide formulation. The optimal use form depends on the intended purpose. Aqueous use forms can be prepared from emulsion concentrates, pastes or wettable powders (e.g., sprayable powders, oil dispersions) by adding water. To prepare emulsions, pastes, or oil dispersions, the substances, as such or dissolved in an oil or solvent, can be homogenized in water by means of a wetter, tackifier, dispersant or emulsifier. However, it is also possible to prepare concentrates that are suitable for dilution with water composed of active substance, wetter, tackifier, dispersant or emulsifier and, if appropriate, solvent or oil.

The active compound concentrations in the ready-to-use preparations can be varied within a relatively wide range. In general, the active compounds are concentrations are from 0.0001% to 10% by weight, preferably from 0.01% to 1% by weight. The ACCase-inhibiting herbicide may also be used successfully in the ultra-low-volume process (ULV), it being possible to apply formulations comprising over 95% by weight of active compound, or even to apply the active compound without additives.

This present invention also provides methods for producing a rice seed or plant by crossing a first parent rice plant with a second parent rice plant, wherein either the first or second parent rice plant is of the line PVL04. In some embodiments, a breeding cross is made to introduce new genetics into the PVL04 progeny (as opposed to a self or a sib cross, made to select among existing genetic alleles). In these embodiments, a population of hybrid rice plants will be produced that, on average, derive 50% of their alleles from cultivar PVL04. The resulting first generation (F1) hybrid rice seeds may be harvested and used to grow plants that express a subset of characteristics from PVL04. Alternatively, a plant of this population may be selected and repeatedly selfed or sibbed with a rice cultivar resulting from successive filial generations. In other embodiments, both the first and second parent rice plants can come from the rice cultivar PVL04. However, advantageously, the rice cultivar is used in crosses with other, different, rice cultivars to produce F1 rice seeds and plants with superior characteristics or desired traits. In some embodiments, the rice cultivar PVL04 is crossed with a second rice plant that is transgenic or gene-edited. Rice cultivar PVL04 may also be crossed with other species, including those of the family Graminaceae, and especially of the genera *Zea, Tripsacum, Croix, Schlerachne, Polytoca, Chionachne*, and *Trilobachne*, of the tribe Maydeae. See the section below titled "Breeding Methods" for a detailed description of breeding techniques that may utilized with the present invention.

In some embodiments, a PVL04 progeny plant is selected that has molecular markers, morphological characteristics, and/or physiological characteristics in common with PVL04. "Marker" or "molecular marker" refers to a readily detectable DNA sequence or nucleotide, which may be genetically closely linked to a gene or locus. Such closely linked markers can be used in MAS (marker assisted selection) of the gene or locus. Types of molecular markers which could be used in accordance with the invention include, but are not necessarily limited to Single Nucleotide Polymorphisms (SNPs), Simple Sequence Length Polymorphisms (SSLPs), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), and Amplified Fragment Length Polymorphisms (AFLPs), insertions and deletions (INDELs) or haplotypes. Molecular markers may be used to identify and/or select progeny that share particular traits with PVL04.

Further, this invention provides methods for introducing one or more desired traits into rice cultivar PVL04. This may be accomplished using traditional breeding methods, such as backcrossing. The trait(s) introduced to cultivar PVL04 may be encoded by a native gene, a transgene, or an edited gene. Here, rice cultivar PVL04 is crossed with a second rice line expressing the desired trait(s) and progeny with both the desired trait and characteristics of PVL04 are selected and crossed. These steps are repeated until plants with both the desired trait(s) and essentially all the physiological and morphological characteristics of PVL04 have been produced.

Alternatively, the desired trait(s) may be introduced into cultivar PVL04 as a transgene via genetic engineering, and optionally, trait "stacking" may be used to introduce more than one trait. In some embodiments, the desired trait(s) is introduced via CRISPR-mediated gene editing or other means available to those of skill in the art to genetically engineer plants or plant cells. The transgene(s) or edited gene(s) may confer at least one trait selected from the following: tolerance to drought, salinity or other growth-limiting environmental factors, herbicide resistance; insect resistance; resistance to bacterial, fungal, or viral disease; modified fatty acid metabolism; modified carbohydrate metabolism; and male sterility. See the sections below titled "Transformation Methods" and "Gene-Editing Methods" for a detailed description of transformation and gene-editing techniques that may utilized with the present invention. The transgenic or gene edited cultivar produced by these methods may be crossed with another cultivar to produce a new transgenic or gene edited cultivar. Alternatively, the transgene(s) or edited gene(s) incorporated by these methods could be moved into another cultivar using traditional backcrossing techniques.

In some embodiments, the desired trait(s) may include, without limitation, pesticidal traits such as Bt Cry and other proteins having pesticidal activity toward coleopteran, lepidopteran, nematode, or other pests; nutritional or nutraceutical traits such as modified oil content or oil profile traits, high protein or high amino acid concentration traits, and other trait types known in the art.

In other embodiments, the desired trait(s) may include tolerance to ACCase inhibitors, such as the "DIMs" (e.g., cycloxydim, sethoxydim, clethodim, or tepraloxydim), the "FOPs" (e.g., clodinafop, diclofop, fluazifop, haloxyfop, or quizalofop), and the "DENs" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, the desired trait(s) may include tolerance to herbicides having other modes of action, for example, chlorophyll/carotenoid pigment inhibitors, cell membrane disruptors, photosynthesis inhibitors, cell division inhibitors, root inhibitors, shoot inhibitors, and combinations thereof.

Herbicide tolerance traits may be selected from those known in the art, including those providing tolerance to: acetohydroxyacid synthase (AHAS) inhibitors; bleaching herbicides such as a 4-hydroxyphenylpyruvate dioxygenase (HPPD) inhibitors or phytoene desaturase (PDS) inhibitors; 5-enolpyruvyl shikimate 3-phosphate synthase (EPSPS) inhibitors such as glyphosate; glutamine synthetase (GS) inhibitors such as glufosinate or bialaphos; auxinic herbicides (e.g., an auxin or auxin mimic, an auxin binding protein inhibitor, or auxin transport inhibitor), e.g., dicamba; lipid biosynthesis inhibitors such as ACCase inhibitors; or oxynil (i.e. bromoxynil or ioxynil) herbicides; protoporphyrinogen-IX oxidase (PPO) inhibitors (e.g., acifluorfen, butafenacil, carfentrazone, pyraflufen (e.g., as pyraflufen-ethyl), saflufenacil, trifludimoxazin, flufenpyr-ethyl, fomesafen, flumiclorac, flumioxazin, lactofen, oxadiargyl, oxadiazon, oxyfluorfen, sulfentrazone); lipid biosynthesis inhibitors such as acetyl CoA carboxylase (ACCase) inhibitors; oxynil (i.e. bromoxynil or ioxynil) herbicides; p-hydroxyphenylpyruvate dioxygenase (4-HPPD) inhibitors; amide(s), e.g., propanil; and the like. Examples of AHAS-inhibitor herbicides include, e.g., imidazolinones, sulfonylureas, triazolopyrimidines, pyrimidinyl(thio)benzoates (including pyrimidinyl(oxy)benzoates), sulfonylaminocarbonyltriazolinones, agronomically acceptable salts and esters thereof, and combinations thereof. Examples of ACCase inhibitor herbicides include, e.g., "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden). Examples of HPPD inhibitors include mesotrione, benzobicyclon, topramezone, tembotrione, and isoxaflutole. Examples of auxinic herbicides include: aminopyralid, dicamba, 2,4-dichlorophenoxyacetic (2,4-D), clopyralid, fluroxypyr, triclopyr or picloram. In addition to dicamba itself, examples of useful dicamba forms include the methyl ester, dimethylamine salt (DMA), diglycoamine salt (DGA), isopropylamine salt (IPA), potassium salt, and sodium salt. In addition to 2,4-D itself, examples of useful 2,4-D forms include the 2-ethylhexyl ester, the iso-octyl ester, the choline salt, the ammonium salt, and the alkylamine salts and alkanolamine salts (specific examples of the latter two including salts with triethylamine (TEA), dimethylamine (DMA), diethylamine, diethanolamine, et al.)

Optionally, any of the disclosed methods may further comprise additional steps involving producing rice seed from the resulting rice plants and/or planting the rice seed.

The present invention encompasses all plants, or parts thereof, produced by the methods described herein, as well as the seeds produced by these plants. Further, any plants derived from rice cultivar PVL04 or produced from a cross using cultivar PVL04 are provided. This includes genetic variants, created either through traditional breeding methods, genetic transformation, or gene editing, as well as plants produced in a male-sterile form. Notably, this includes gene-converted plants developed by backcrossing and $F_1$ hybrid plants. Any of the seeds, plants, or plant parts provided may be utilized for human food, livestock feed, and as a raw material in industry.

The present invention also encompasses progeny of rice cultivar PVL04 comprising a combination of at least two PVL04 traits selected from those listed in the Tables and Detailed Description of the Invention, wherein the progeny rice plant is not significantly different from PVL04 for said traits, as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of PVL04. Alternatively, progeny may be identified through their filial relationship with rice cultivar PVL04 (e.g., as being within a certain number of breeding crosses of rice cultivar PVL04). For example, progeny produced by the methods described herein may be within 1, 2, 3, 4, or 5 breeding crosses of rice cultivar PVL04.

Tissue Culture

The present invention provides tissue cultures of regenerable cells or protoplasts produced from rice cultivar PVL04. As is well known in the art, tissue culture of rice can be used for the in vitro regeneration of a rice plant. Thus, such cells and protoplasts may be used to produce plants having the physiological and morphological characteristics of rice variety PVL04. The rice plants regenerated by these methods are also encompassed by the present invention.

As used herein, the term "tissue culture" describes a composition comprising isolated cells or a collection of such cells organized into parts of a plant. Exemplary tissues for culture include protoplasts, calli, plant clumps, and plant cells that can be grown in culture, or parts of plants, such as embryos, pollen, flowers, seeds, pods, leaves, stems, roots, root tips, anthers, nodes, and buds. Culture of various rice tissues and regeneration of plants therefrom is well known in the art.

Breeding Methods

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low or high temperatures, herbicide resistance, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar PVL04 in any plant breeding method is encompassed by the present invention. The choice of a breeding or selection method will depend on several factors, including the mode of plant reproduction, the heritability of the trait(s) being improved, and the type of cultivar used commercially (e.g., F1 hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the $F_4$ generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of rice cultivar PVL04 in which one or more additional traits have been transferred. While such traits may be selected for using traditional breeding methods, they may also be introduced as transgenes via genetic engineering. "Transgenes" include both foreign genes and additional or modified versions of native genes. Plants can be genetically engineered to have a wide variety of traits of agronomic interest including, without limitation, tolerance to drought, salinity or other growth-limiting environmental factors, male sterility, waxy starch, herbicide resistance, resistance for bacterial, fungal, or viral disease, insect resistance, male fertility, enhanced nutritional quality, modified fatty acid metabolism, modified carbohydrate metabolism, industrial usage, yield stability, and yield enhancement. Many examples of genes that confer such traits have been described in the literature and are well known in the art. For example, the transgene may confer resistance to an herbicide selected from the group consisting of: quizalofop-ethyl, aryloxyphenoxy-propionate, glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The vector may be a plasmid, and can be used alone or in combination with other plasmids. The vector may include genes encoding multiple traits (i.e., "stacked" traits).

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and Green Fluorescent Protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific", "cell type-specific", "inducible", or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glick, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glick, et al., (Eds. pp. 67-88 CRC Press, 1993); and by Phillips, et al., "Cell-Tissue Culture and In-Vitro Manipulation" in *Corn & Corn Improvement,* 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber, et al., supra.

Gene-Editing Methods

The present invention provides plants and seeds of rice cultivar PVL04 in which additional traits have been added. The desired trait(s) may be encoded by an edited gene or genes. The present invention provides plants or plant parts comprising an edited gene or genes. As used here, a plant is "gene-edited" if the plant comprises one or more cells that comprise an edited gene.

Gene editing may involve the introductions of deletions or insertions into a native gene, integrations of exogenous DNA, gene correction, and/or gene mutation. Gene editing can be used to introduce a transgene into the genome; to silence, reduce, or increase the expression of a native gene; or to modify the product produced by a native gene. Gene editing is performed using several methods that are known in the art. Using these methods, new genetic material may be introduced into the cell directly (i.e., via injection, encapsulation, or electroporation) or delivered via another cell or a virus that is then fused with the cell. Genetic engineering methods may involve use of engineered nucleases (e.g., meganucleases, zinc finger nucleases (ZFN), transcription activator-like effector nucleases (TALENs), and the Cas9-guideRNA system (adapted from CRISPR). In some embodiments, genetic engineering involves altering the nuclear genome of the cell. When new genetic material is introduced to the nuclear genome, it can be inserted randomly or targeted to a specific location (e.g., via homologous recombination or CRISPR-based gRNA targeting). In other embodiments, the engineered cell may harbor a vector comprising a target gene that is expressed independently of the nuclear genome.

REFERENCES

Browning, J. E. "Agglomeration: growing larger in applications and technology." Chemical Engineering, Dec. 4, 1967, pp. 147-48.

D. A. Knowles, "Chemistry and Technology of Agrochemical Formulations", Dordrecht, Kluwer Academic Publishers (ISBN 0-7514-0443-8), 1998.

Fehr and Walt, Principles of Cultivar Development, 1987. p. 261-286.

Gruber, et al., "Vectors for Plant Transformation." in: Glick, et al., Methods in Plant Molecular Biology & Biotechnology, (Boca Raton, FL, CRC Press, 1993), pp. 89-119.

Hance et al., Weed Control Handbook, 8th Ed. Oxford, Blackwell Scientific Publications, 1989.

Horsch, R. B., et al. "A simple and general method for hybridization revealed the expected." Science 227:1229-1231. (1985).

Klingman, G. C. and Noordhoff, L. J., "Weed Control as a Science", New York, John Wiley and Sons, Inc., 1961.

Maki et al., "Procedures for Introducing Foreign DNA into Plant." in: Glick et al., Methods in Plant Molecular Biology & Biotechnology, (Boca Raton, FL, CRC Press, 1993), pp. 67-88.

Mollet, H., Grubemann, A., "Formulation technology", Weinheim, Germany, Wiley VCH Verlag GmbH, 2001.

Perry, R. H. et al., Perry's Chemical Engineer's Handbook, 4th Ed., New York, McGraw-Hill, 1963, pp. 8-57.

Phillips et al., "Cell-Tissue Culture and In-Vitro Manipulation." in: Sprague, G. F. and Dudley, J. W., Corn & Corn Improvement, Vol. 18, 3rd Edition (1988).

Webb, B. D., C. N. Bollich, H. L. Carnahan, K. A. Kuenzel., and K. S. McKenize. 1985. Utilization characteristics and qualities of United States rice. p. 25-35. In: Rice grain quality and marketing. IRRI, Manila, Philippines

DEPOSIT INFORMATION

A deposit of the University of Arkansas Division of Agriculture Rice Research and Extension Center proprietary rice cultivar 'PVL04' disclosed above and recited in the appended claims has been made with the Provasoli-Guillard National Center for Marine Algae and Microbiota (NCMA), Bigelow Laboratory for Ocean Sciences, 60 Bigelow Drive, East Boothbay, ME 04544. The date of deposit was Jan. 8, 2025. The deposit of 625 seeds was taken from the same deposit maintained by the University of Arkansas Division of Agriculture Rice Research and Extension Center (2900 Hwy 130 E., Stuttgart, AR 72160) since prior to the filing date of this application. All restrictions will be irrevocably removed upon granting of a patent, and the deposit is intended to meet all of the requirements of 37 C.F.R. §§ 1.801-1.809. The Accession Number provided by the International Depositary Authority is 202501001. The deposit will be maintained in the depository for a period of thirty years, or five years after the last request, or for the enforceable life of the patent, whichever is longer, and will be replaced as necessary during that period.

What is claimed is:

1. A rice seed of the cultivar 'PVL04', a representative sample of seed of said cultivar having been deposited under National Center for Marine Algae and Microbiota International Depositary Authority Accession No. 202501001.

2. A rice plant, or a part thereof, produced by growing the seed of claim 1.

3. The rice plant of claim 2, wherein said plant is treated with an agronomically acceptable herbicide treatment composition.

4. The rice plant of claim 3, wherein the herbicide treatment composition comprises Acetyl CoA Carboxylase (ACCase)-inhibiting herbicide.

5. The rice plant of claim 4, wherein said ACCase-inhibiting herbicide is selected from the group consisting of aryloxyphenoxy-propionate herbicides, cyclohexanedione herbicides, phenylpyrazoline herbicides, an agronomically acceptable salt or ester of one of these, combinations, and mixtures thereof.

6. The rice plant of claim 5, wherein said ACCase-inhibiting herbicide comprises an aryloxyphenoxy-propionate herbicide or a mixture of two or more aryloxyphenoxy-propionate herbicides.

7. The rice plant of claim 5, wherein the aryloxyphenoxy-propionate herbicide is selected from the group consisting of prop-2-ynyl (R)-2-[4-(5-chloro-3-fluoro-2-pyridyloxy)phenoxy]propionate, 2-[4-(4-chlorophenoxy)phenoxy]propionic acid, butyl (R)-2-[4-(4-cyano-2-fluorophenoxy)phenoxy]propionate, methyl (RS)-2-(4-(2,4-dichlorophenoxy)phenoxy)propionate, ethyl (RS)-2-[4-(6-chloro-1,3-benzoxazol-2-yloxy)phenoxy]propionate, (RS)-2-[4-(6-chloro-1,3-benzothiazol-2-yloxy)phenoxy]propionic acid, butyl (RS)-2-{4-[5-(trifluoromethyl)-2-pyridyloxy]phenoxy}propionate, methyl 2-[4-[3-chloro-5-(trifluoromethyl)pyridin-2-yl]oxyphenoxy]propanoate, (RS)-2-[2-[4-(3,5-dichloro-2-pyridyloxy)phenoxy]propionyl]-1,2-oxazolidine, (R)-2-[4-(6-chloro-1,3-benzoxazol-2-yloxy)phenoxy]-2'-fluoro-N-methylpropionanilide, ethyl (R)-2-[4-(6-chloroquinoxalin-2-yloxy)phenoxy]propionate, clodinafop-propargyl, clofop, cyhalofop-butyl, diclofop-methyl, fenoxaprop-ethyl, fenthiaprop, fluazifop-butyl, haloxyfop-methyl, isoxapyrifop, metamifop, quizalofop-ethyl herbicides, and mixtures thereof.

8. Pollen or an ovule of the plant of claim 2.

9. A method for producing rice plants, said method comprising planting a plurality of rice seeds as recited in claim 1 under conditions favorable for the growth of rice plants.

10. The method of claim 9, further comprising the step of producing rice seed from the resulting rice plants.

11. An $F_1$ rice seed produced by the method of claim 10.

12. A method for combating undesired vegetation or controlling weeds in the vicinity of a rice plant of rice cultivar 'PVL04', comprising applying an effective amount of at least one ACCase-inhibiting herbicide to the weeds and to the rice plant, a representative sample of seed of said cultivar having been deposited under National Center for Marine Algae and Microbiota International Depositary Authority Accession No. 202501001.

13. The method of claim 12, wherein said ACCase-inhibiting herbicide is selected from the group consisting of aryloxyphenoxy-propionate herbicides, cyclohexanedione herbicides, phenylpyrazoline, an agronomically acceptable salt thereof, an ester thereof, combinations, and mixtures thereof.

14. The method of claim 13, wherein said aryloxyphenoxy-propionate herbicide is selected from the group consisting of prop-2-ynyl (R)-2-[4-(5-chloro-3-fluoro-2-pyridyloxy)phenoxy]propionate, 2-[4-(4-chlorophenoxy)phenoxy]propionic acid, butyl (R)-2-[4-(4-cyano-2-fluorophenoxy)phenoxy]propionate, methyl (RS)-2-(4-(2,4-dichlorophenoxy)phenoxy)propionate, ethyl (RS)-2-[4-(6-chloro-1,3-benzoxazol-2-yloxy)phenoxy]propionate, (RS)-2-[4-(6-chloro-1,3-benzothiazol-2-yloxy)phenoxy]propionic acid, butyl (RS)-2-{4-[5-(trifluoromethyl)-2-pyridyloxy]phenoxy}propionate, methyl 2-[4-[3-chloro-5-(trifluoromethyl)pyridin-2-yl]oxyphenoxy]propanoate, (RS)-2-[2-[4-(3,5-dichloro-2-pyridyloxy)phenoxy]propionyl]-1,2-oxazolidine, (R)-2-[4-(6-chloro-1,3-benzoxazol-2-yloxy)phenoxy]-2'-fluoro-N-methylpropionanilide, ethyl (R)-2-[4-(6-chloroquinoxalin-2-yloxy)phenoxy]propionate, clodinafop-propargyl, clofop, cyhalofop-butyl, diclofop-methyl, fenoxaprop-ethyl, fenthiaprop, fluazifop-butyl, haloxyfop-methyl, isoxapyrifop, metamifop, quizalofop-ethyl, and mixtures thereof.

15. A tissue culture of regenerable cells or protoplasts produced from the rice plant, or the plant part of claim 2.

16. The tissue culture of claim 15, wherein said cells or protoplasts are produced from a tissue selected from the group consisting of embryos, meristematic cells, pollen, leaves, anthers, roots, root tips, pistils, anthers, cotyledon, hypocotyl, glumes, panicles, flowers, seeds, stems, nodes, and buds.

17. A rice plant regenerated from the tissue culture of claim 15, said rice plant having all the morphological and physiological characteristics of 'PVL04'.

18. A method for producing herbicide-resistant $F_1$ hybrid rice, said method comprising crossing a first parent rice plant with a second parent rice plant, wherein the first parent rice plant is the rice plant of claim 2, and the second parent rice plant is a different cultivar, and optionally wherein the second parent rice plant is not resistant to an herbicide.

19. The method of claim 18, further comprising selecting for a progeny rice plant that is resistant to at least one ACCase-inhibiting herbicide to produce an herbicide resistant $F_1$ hybrid rice plant.

20. The method of claim 19, wherein said ACCase-inhibiting herbicide is an aryloxyphenoxy-propionate herbicide or a mixture of two or more aryloxyphenoxy-propionate herbicides.

21. An herbicide-resistant $F_1$ hybrid rice plant or plant part thereof, wherein said plant is produced by the method of claim 18.

22. The method of claim 18, further comprising the step of producing rice seed from the resulting rice plants.

23. The method of claim 18, wherein the second parent rice plant is transgenic or gene-edited.

24. A method comprising transforming the rice plant of claim 2 or cell thereof with a transgene, wherein the transgene confers a trait selected from the group consisting of: tolerance to drought or salinity; herbicide resistance; insect resistance; resistance to bacterial, fungal or viral disease; modified fatty acid metabolism; modified carbohydrate metabolism; and male sterility.

25. A rice plant or part thereof, produced by the method of claim 24, wherein the plant comprises said transgene and otherwise has all of the morphological and physiological characteristics of rice cultivar 'PVL04'.

26. A method of introducing a desired trait into rice cultivar 'PVL04', said method comprising the steps of:

(a) crossing a plant as recited in claim 2 with a plant of another rice line expressing the desired trait, to produce progeny seeds;

(b) growing the progeny seeds to produce progeny plants and selecting the progeny plants that express the desired trait, to produce selected progeny plants;

(c) crossing the selected progeny plants with plants as recited in claim 2 to produce new progeny plants;

(d) selecting the new progeny plants that express both the desired trait and some or all of the physiological and morphological characteristics of rice cultivar 'PVL04', to produce new selected progeny plants; and (e) repeating steps (c) and (d) three or more times in succession, to produce selected higher generation backcross progeny plants that express both the desired trait and essentially all of the physiological and morphological characteristics of rice cultivar 'PVL04', as described in the specification, determined at a 5% significance level, when grown in the same environmental conditions; and wherein the selected plants express the ACCase herbicide resistance characteristics of 'PVL04'.

* * * * *